United States Patent [19]

Jarreau et al.

[11] 4,325,879
[45] Apr. 20, 1982

[54] NEW AMINO-14 STEROID DERIVATIVES AND PROCESS FOR PREPARATION OF THE SAME

[75] Inventors: François-Xavier Jarreau, Versailles; Jean J. Koenig, Vernou la Celle, both of France

[73] Assignee: Etablissements Nativelle S.A., Paris, France

[21] Appl. No.: 182,546

[22] Filed: Aug. 29, 1980

[30] Foreign Application Priority Data

Aug. 31, 1979 [FR] France .................................. 79 21844

[51] Int. Cl.³ .................. C07C 117/00; C07C 121/86
[52] U.S. Cl. ................................ 260/349; 260/397.1; 260/397.5
[58] Field of Search ...................... /Steroids MS File; 260/349

[56] References Cited

U.S. PATENT DOCUMENTS 3,558,673 1/1971 De Ruggieri et al. .......... 260/397.47

Primary Examiner—Elbert L. Roberts

Attorney, Agent, or Firm—Sughrue, Mion, Zinn, Macpeak & Seas

[57] ABSTRACT

The invention relates to medicinally useful steroid derivatives, particularly amino-14 steroids substituted at the 17-position by a functional group represented by the general formula:

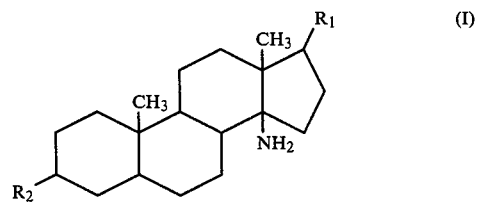

wherein $R_1$ is a hydroxy, hydroxyalkyl, alkoxy, acyloxy, carboxy or carbalkoxy group, or a hydrogen atom, and $R_2$ is a hydroxy, alkoxy, or acyloxy group. These amino-14 steroids are prepared from the corresponding hydroxy-14 steroids, by the action of hydrazoic acid in the presence of boron trifluoride etherate to form the azido-14 derivative which is reduced.

10 Claims, No Drawings

NEW AMINO-14 STEROID DERIVATIVES AND PROCESS FOR PREPARATION OF THE SAME

BACKGROUND OF THE INVENTION

1. Field of the Invention

The present invention relates to new steroid derivative compounds, and in particular, relates to amino-14 steroids substituted at the 17-position by a functional group, as well as to a process for their preparation.

2. Description of the Prior Art

It is known to transform a tertiary alcohol function into an azide, by the action of hydrazoic acid in the presence of boron trifluoride etherate in an aromatic medium. For example, the synthesis of azido-14 pregnanes and amino-14 pregnanes by such a process is described by Astier et al., *Bull. Soc. Chim.*, 1976, 1581.

SUMMARY OF THE INVENTION

An object of the present invention is to provide new derivative compounds of amino-14 steroids, for possible use as medicines, or as intermediates in the manufacture of compounds useful as medicines.

The new compounds of the present invention can be represented by the following general formula (I):

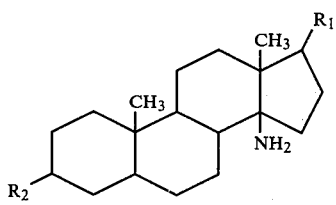

wherein $R_1$ represents a hydroxy, hydroxyalkyl, alkoxy, acyloxy, carboxy or carbalkoxy group, or a hydrogen atom, and $R_2$ represents a hydroxy, alkoxy or acyloxy group.

The compounds of the general formula (I) above can be prepared from alcohols of the general formula (II):

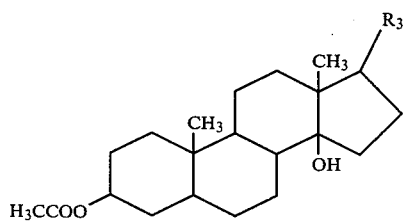

wherein $R_3$ is a carbalkoxy or acyloxy group, or a hydrogen atom, by the action of hydrazoic acid in the presence of boron trifluoride etherate in an appropriate solvent to form an azido-14 derivative which is then reduced to form an amino-14 steroid of the general formula (I).

DETAILED DESCRIPTION OF THE INVENTION

The starting materials of the general formula (II), and in particular acetoxy-3β hydroxy-14β androstane and diacetoxy-3β, 17β hydroxy-14β androstane, can easily be obtained from hydroxy-3 androstanone-17 prepared in accordance with the method described in N. Danielli et al., *Tetrahedron*, 23, 715 (1967); likewise acetoxy-3β hydroxy-14β methyl 5β-etianate can easily be obtained as described in F. Hunziker et al., *Helv. Chim. Acta*, 28, 1472 (1945).

According to the process of the present invention, an alcohol of general formula (II) is treated with hydrazoic acid in excess, in a solvent such as benzene or toluene, in the presence of boron trifluoride etherate. The reaction is preferably carried out at ambient temperature.

Under these conditions, the alcohol is transformed into the corresponding azide, which can be represented by the general formula (II) but where the OH group at the 14-position is replaced by an $N_3$ group.

After extraction of the azide, and purification as necessary, a reduction reaction is carried out to form the amino-14 steroid of the general formula (I).

The reduction can be carried out by hydrogenation of the azide in the presence of a catalyst such as Lindlar's catalyst. A hydride, such as lithium-aluminum hydride, can be used as a reducing agent in a solvent such as tetrahydrofuran or an ether. The azide to amine reduction can also be carried out using usual suitable reducing agents, such as sulfurated reducing agents, metallic reducing agents, etc. The choice of the method of reduction enables the reaction to be oriented preferentially towards amino-14 steroids substituted by a hydroxy or hydroxyalkyl group, in the case of the lithium-aluminum hydride method, or towards other derivatives substituted by an acyloxy or carbalkoxy, by using the first method. In addition, the carbalkoxy group can easily be transformed into a carboxyl group by usual processes.

Among the compounds of general formula (I), the invention relates preferably to those in which $R_1$ is a hydroxy, hydroxymethyl, acetoxy or carbomethoxy group or a hydrogen atom, and $R_2$ is a hydroxy or acetoxy group.

The invention also relates to salts of the amino-14 steroids of the general formula (I), obtained in the usual manner, by reaction, in substantially stochiometric proportions, with an appropriate acid, such as hydrochloric, sulfuric, acetic, phosphoric, oxalic, lactic, tartaric, maleic acid, etc., preferably in a compatible solvent.

The invention also covers new azido-14 compounds, represented by the general formula (III) below, as intermediates in the synthesis of the amino-14 steroids of the formula (I):

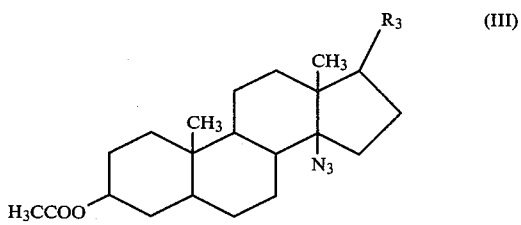

wherein $R_3$ represents a hydrogen atom or an acyloxy or carbalkoxy group, preferably an acetoxy or carboxymethyl group.

The following examples are given to illustrate the invention in more detail, without limiting the scope of the present invention.

EXAMPLE 1

Acetoxy-3β azido-14β methyl etianate 31.2 g of acetoxy-3β hydroxy-14β 5β-methyl etianate, prepared by the method described in F. Hunziker et al., Helv. Chim. Acta, 28, 1472 (1945), were placed in solution in 100 ml of benzene in a 3 l flask. 1 l of an aromatic hydrazoic acid solution, in an appreciably molar concentration, was added progressively, then 80 ml of boron trifluoride etherate, at ambient temperature was added. The reaction was carried out by maintaining the medium under agitation for 15 min.

The medium was flooded with ice-cold ammonia, the aromatic phase was washed with a sodium bicarbonate solution and then extraction was carried out using methylene chloride. After purification by distillation and recrystallization in acetone 16.1 g of acetoxy-3$\beta$ azido-14$\beta$ methyl etianate was obtained (yield 50%).

Melting point MP=204°–205° C. (acetone)

NMR spectrum (CDCl$_3$) $\delta$=0.96 (3H,s) 1.00 (3H,s) 2.03 (3H,s) 0.7 to 2.4 (21H) 2.53 (1H,t,J=5) 3,68 (3H,s) 5.07 (1H) ppm. IR spectrum: $\nu$=2110, 2095, 1725 cm$^{-1}$ (Nujol).

EXAMPLE 2

Diacetoxy-3$\beta$, 17$\beta$ azido-14$\beta$ 5$\beta$-androstane

Using the same procedure as in Example 1, starting from diacetoxy-3$\beta$, 17$\beta$ hydroxy-14$\beta$ 5$\beta$-androstane prepared by the method described in N. Danielli et al., Tetrahedron, 23, 715 (1967), the yield of the reaction was practically quantitative.

NMR spectrum (CDCl$_3$) $\delta$=0.98 (3H,s) 1.03 (3H,s) 0.7 to 2.6 (21H) 2.05 (6H,s) 5.03 (1H) 5.06 (1H) ppm.

EXAMPLE 3

Acetoxy-3$\beta$ azido-14$\beta$ androstane

Using the procedures of Example 1, acetoxy-3$\beta$ hydroxy-14$\beta$ androstane was treated with an aromatic solution of hydrazoic acid and boron trifluoride etherate.

An oily residue was obtained which was purified by column chromatography. After purification, white crystals of acetoxy-3$\beta$ azido-14$\beta$ androstane with a yield of 60% were obtained.

IR spectrum $\nu$=2105, 2080, 1725, 1230 and 1020 cm$^{-1}$ (Nujol).

NMR spectrum (CDCl$_3$) $\delta$=0.96 (3H,s) 1.01 (3H,s) 0.8 to 2.8 (23H) 2.04 (3H,s) 5.08 (1H) ppm.

EXAMPLE 4

Hydroxy-3$\beta$ amino-14$\beta$ androstane 1 g of acetoxy-3$\beta$ azido-14$\beta$ androstane obtained as described in Example 3, was treated in solution in 100 ml of tetrahydrofuran with 7 g with 0.5 g of lithium-aluminum hydride. This was flooded with ethyl acetate and then filtered and the filtrate was distilled. The residue was washed with ethyl acetate and then extracted with 0.5 N hydrochloric acid. After rendering the aqueous phase alkaline with ammonia and further extraction followed by washing, drying and distillation, 0.7 g of hydroxy-3$\beta$ amino-14$\beta$ androstane was obtained (yield 78%).

IR spectrum: $\nu$=2600 to 3600, 1585 and 1030 cm$^{-1}$ (CHCl$_3$ film).

NMR spectrum (CDCl$_3$) $\delta$=0.93 (6H,s) 0.7 to 2.3 (23H) 1.6 (3H mobile) 4.10 (1H) ppm.

CCM (CHCl$_3$-MeOH-NH$_4$OH; 90-10-1) Rf=0.4.

The corresponding hydrochloride, with a melting point of >260° C. (dec.), was prepared by the usual techniques.

EXAMPLE 5

Acetoxy-3$\beta$ amino-14$\beta$ methyl etianate 0.25 g of 5% palladium on calcium carbonate (Lindlard's catalyst) was added to 0.5 g of the azide obtained as described in Example 1 in solution in 100 ml of ethanol. The reduction reaction was conducted for 20 hours, under agitation, in a hydrogen atomosphere.

After filtration and distillation, the residue was recrystallized in ethanol to obtain 0.3 g of acetoxy-3$\beta$ amino-14$\beta$ methyl etianate crystals (yield 63%).

By taking up the mother liquors with water to which citric acid had been added and by carrying out a further extraction followed by crystallization, 0.1 g of additional crystals was obtained, bringing the yield to 85%.

Melting point=196°–197° C. (ethanol).

IR spectrum $\nu$=3430, 3370, 3410, 1725, 1250, 1230, 1170, 1020 cm$^{-1}$ (Nujol) 3360, 3300, 1720 (strong), 1600, 1260, 1170, 1020 cm$^{-1}$ (CHCl$_3$).

CCM (CH$_2$Cl$_2$-MeOH-NH$_4$OH, 96-4-0.4) Rf=0.55.

NMR spectrum (CDCl$_3$) $\delta$=0.96 (3H,s) 0.98 (3H,s) 2.03 (3H,s) 0.7 to 2.3 (21H) 2.46 (1H+2H mobiles) 3.65 (3H,s) 5.03 (1H) ppm.

EXAMPLE 6

Dihydroxy-3$\beta$, 20 amino-14$\beta$ nor-21-pregnane 0.4 g of azide obtained as described in Example 1 in solution in 10 ml of anhydrous tetrahydrofuran was treated with 200 mg of lithium-aluminum hydride added progressively thereto. The reaction took place at ambient temperature. When completed, the product was hydrolyzed and flooded with 100 ml of ethyl acetate. After filtration and distillation, the residue was washed with diethyl ether and then recrystallized in ethyl acetate.

Dihydroxy-3$\beta$, 20 amino-14$\beta$ nor-21-pregnane was obtained with a yield of 52% in the form of pure crystals.

NMR spectrum (CDCl$_3$) $\delta$=0.91 (3H,s) 0.96 (3H,s) 0.7 to 2.3 (22H) 2.7 to 3.5 (4H mobiles) 3.30 (1H,d,J=11) 3.68 (1H,d,J=11) 4.10 (1H) ppm.

IR spectrum $\nu$=3100 to 3600, 3390, 3290, 2200 to 3100 (2660), 1595, 1520, 1110, 1030 cm$^{-1}$ (Nujol)

Melting point=217°–218° C.

EXAMPLE 7

Using usual techniques, monoacetylated and diacetylated derivatives of dihdyroxy-3,$\beta$ 20-amino-14$\beta$ nor-21 pregnane were prepared as follows.

Hydroxy-3$\beta$ acetoxy-20 amino-14$\beta$ nor-21 pregnane.

Melting point=80° C.

IR spectrum $\nu$=1725, 1650, 1600 cm$^{-1}$ (Nujol).

Acetoxy-3$\beta$ hydroxy 20 acetamido-14$\beta$ nor-21 pregnane.

Melting point=232° C.

IR spectrum $\nu$=3220, 1735, 1650, 1575 cm$^{-1}$ (Nujol) and diacetoxy-3$\beta$, 20 amino-14$\beta$ nor-21 pregnane.

IR spectrum $\nu$=3400, 1740, 1730 cm$^{-1}$ (Nujol).

EXAMPLE 8

Dihydroxy-3$\beta$, 17$\beta$ amino-14$\beta$ 5$\beta$-androstane

The process of Example 6 was employed, with the azide of Example 1 being replaced by the azide of Example 2.

In this manner dihydroxy-3$\beta$, 17$\beta$ amino-14$\beta$ 5$\beta$-androstane was obtained with a yield of 60%.

IR spectrum: ν=2500 to 3700, 1590, 1035 cm⁻¹ (Nujol).

CCM (CHCl₃-MeOH-NH₄OH, 90-10-1) Rf=0.35.

By the action of hydrochloric acid, using usual techniques, dihydroxy-3β 17β amino-14β 5β-androstane hydrochloride was prepared.

Melting point=260° C. (decomposition-Ethanol).

NMR spectrum (CD₃OD) δ=0.98 (6H,s) 0.7 to 2.4 (21H) 3.6 (1H) 4.06 (1H) ppm.

EXAMPLE 9

Diacetoxy-3β, 17β amino-14β 5β-androstane

The process of Example 5 was used, with the azide of Example 1 being replaced by the azide of Example 2.

In this manner diacetoxy-3β, 17β amino-14β 5β-androstane was obtained with a yield of 50%.

IR spectrum ν=3000 to 3600, 3430, 3385, 3310, 3010.

NMR spectrum (CDCl₃) δ=0.95 (6H,s) 2.03 (6H,s) 0.7 to 2.7 (21H+2H mobiles) 5.10 (1H) 5.20 (1H) ppm.

EXAMPLE 10

Acetoxy-3β azido-14β iso-17 methyl etinate 4 g of acetoxy-3β hydroxy-14β iso-17 methyl etianate, the isomer of the starting compound of Example 1, obtained by the same method, was dissolved in 200 ml of an appreciably molar solution of hydrazoic acid in benzene. 20 ml of boron trifluoride etherate were added under agitation at ambient temperature. The reaction medium was maintained under agitation for 15 min.

This was flooded with ice-cold ammonia, the organic phase were washed with a sodium bicarbonate solution and extracted with methylene chloride. After distillation a white residue was obtained which was purified by crystallization in methanol.

In this manner 34 g of acetoxy-3β azido-14β iso-17 methyl etianate was obtained with a yield of 77%.

Melting point=157°–158° C.

IR spectrum ν=2100, 1730, 1720 cm⁻¹ (Nujol).

NMR spectrum (CHCl₃) δ=0.96 (3H,s) 1.15 (3H,s) 2.03 (3H,s) 0.7 to 2.6 (21H) 2.7 to 3.5 (1H, m) 3.66 (3H,s) 5.06 (1H) ppm.

EXAMPLE 11

Acetoxy-3β amino-14β iso-17 methyl etianate

The process of Example 5 was used, with the azide of Example 1 being replaced by that of Example 10.

In this manner acetoxy-3β amino-14β iso-17 methyl etianate was obtained in the form of pure crystals with a yield of 63%.

Melting point=165°–166° C.

IR spectrum ν=3100 to 3600, 1730, 1725 cm⁻¹ (Nujol).

NMR spectrum (CDCl₃) δ=0.93 (3H,s) 1.10 (3H,s) 2.01 (3H,s) 0.7 to 2.5 (21H+2H mobiles) 3.1 (1H) 3.63 (3H,s) 5.02 (1H).

EXAMPLE 12

Dihydroxy-3β, 20 amino-14β nor-21 (17α) pregnane

The process of Example 6 was used, with the azide of Example 1 being replaced by that of Example 8.

In this manner, after withdrawal of the mother liquors, pure crystals of dihyroxy-3β, 20 amino-14β nor-21 (17α) pregnane were obtained with a yield of 65%.

Melting point=216°–218° C.

IR spectrum ν=2500 to 3600, 1575 cm⁻¹ (Nujol).

NMR spectrum (CDCl₃+CD₃OD) δ=0.93 (3H,s) 0.98 (3H,s) 0.7 to 2.7 (22H) 3.50 (2H) 4.05 (1H) 4.0 (4H mobiles) ppm.

Pharmacological and toxicical experiments carried out on the compounds of this invention have shown evidence of interesting properties, namely inotropic activity, enabling their therapeutic application in the treatment of cardiac disorders. Further the compounds of the present invention are expected to be useful as intermediates in the preparation of useful derivatives.

What is claimed is:

1. Amino-14 steroid derivatives of the general formula (I):

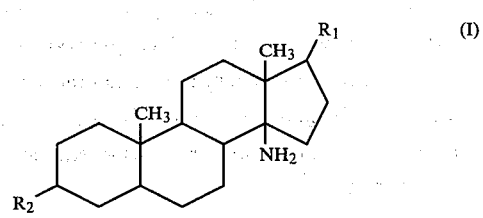

wherein R₁ represents a hydrogen atom, a hydroxy, hydroxyalkyl, alkoxy, acyloxy, carboxy or carbalkoxy group, and R₂ represents a hydroxy, alkoxy or acyloxy group, and the acid addition salts thereof.

2. The amino-14 steroid derivatives of claim 1, wherein R₁ is a hydroxy, hydroxymethyl, acetoxy or carbomethoxy group or a hydrogen atom.

3. The amino-14 steroid derivatives of claim 1, wherein R₂ is a hydroxy or acetoxy group.

4. The amino-14 steroid derivatives of claim 1, wherein said derivatives are selected from the group consisting of:
   acetoxy-3β amino-14β methyl etianate,
   hydroxy-3β amino-14β androstane,
   dihydroxy-3β, 20 amino-14β nor-21-pregnane,
   hydroxy-3β acetoxy-20 amino-14β nor-21 pregnane,
   diacetoxy-3β 20 amino-14β nor-21 pregnane,
   dihydroxy-3β, 17β amino-14β 5β-androstane,
   diacetoxy-3β, 17β amino-14β 5β-androstane,
   acetoxy-3β amino-14β iso-17 methyl etianate, and
   dihydroxy-3β, 20 amino-14β nor-21 (17α) pregnane.

5. A process for the preparation of amino-14 steroid derivatives of the general formula (I) of claim 1

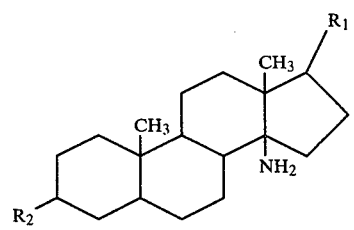

wherein R₁ is a hydrogen atom or a hydroxy, hydroxyalkyl, alkoxy, acyloxy, carboxy or carbalkoxy group and R₂ is a hydroxy, alkoxy or acyloxy group, comprising treating an alcohol of the general formula (II)

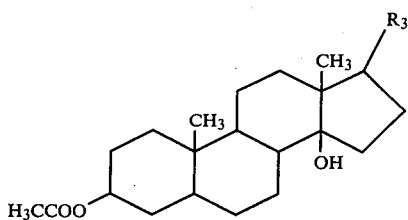

wherein $R_3$ is a carbalkoxy or acyloxy group, or a hydrogen atom, with hydrazoic acid in the presence of boron trifluoride etherate, to form the corresponding azido-14 steroid, and reducing the azido-14 steroid to form the amino-14 steroid of the general formula (I).

6. The process of claim 5, wherein the treating of the alcohol of the general formula (II) with hydrazoic acid in the presence of boron trifluoride etherate is in benzene or toluene.

7. The process of claims 5 or 6, wherein the hydrazoic acid is used in excess with respect to the alcohol of the general formula (II).

8. The process of claim 5, wherein the reducing of the azido-14 steroid is by hydrogenating the azido-14 steroid in the presence of Lindlard's catalyst, or by reducing the azido-14 steroid with lithium-aluminum hydride.

9. The process of claims 5, 6 or 8, wherein the process is conducted at ambient temperature.

10. Amino-14 steroids represented by the general formula (III):

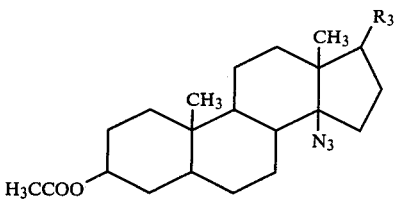

wherein $R_3$ represents an acyloxy or carbalkoxy group or a hydrogen atom.

* * * * *